US012697029B2

(12) United States Patent (10) Patent No.: US 12,697,029 B2
Moon et al. (45) Date of Patent: *Aug. 4, 2026

(54) METHOD AND APPARATUS FOR CORRECTING ERROR OF OPTICAL SENSOR, AND APPARATUS FOR ESTIMATING BIOMETRIC INFORMATION

(71) Applicant: SAMSUNG ELECTRONICS CO., LTD., Suwon-si (KR)

(72) Inventors: Hyun Seok Moon, Hwaseong-si (KR); Sang Kyu Kim, Yongin-si (KR); Yoon Jae Kim, Seoul (KR); Jin Young Park, Hwaseong-si (KR); Sung Mo Ahn, Yongin-si (KR); Kun Sun Eom, Yongin-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 665 days.

This patent is subject to a terminal disclaimer.

(21) Appl. No.: 18/126,156

(22) Filed: Mar. 24, 2023

(65) Prior Publication Data

US 2023/0233084 A1 Jul. 27, 2023

Related U.S. Application Data

(63) Continuation of application No. PCT/KR2021/012886, filed on Sep. 17, 2021.

(30) Foreign Application Priority Data

Sep. 25, 2020 (KR) ........................ 10-2020-0124753
Sep. 17, 2021 (KR) ........................ 10-2021-0124943

(51) Int. Cl.
*A61B 5/00* (2006.01)

(52) U.S. Cl.
CPC .... *A61B 5/0059* (2013.01); *A61B 2560/0223* (2013.01)

(58) Field of Classification Search
CPC . A61B 5/0059; A61B 2560/0223; A61B 5/02; A61B 5/1495; A61B 5/1455; G01N 21/27
See application file for complete search history.

(56) References Cited

U.S. PATENT DOCUMENTS 6,049,727 A 4/2000 Crothall
7,312,854 B2 12/2007 Sugiyama et al.
(Continued)

FOREIGN PATENT DOCUMENTS

CN 103267728 A 8/2013
JP 2006-226851 A 8/2006
(Continued)

OTHER PUBLICATIONS

English translation of JP-7516773-B2 (Year: 2024).*
(Continued)

*Primary Examiner* — Tarifur R Chowdhury
*Assistant Examiner* — Carlos Perez-Guzman
(74) *Attorney, Agent, or Firm* — Sughrue Mion, PLLC

(57) ABSTRACT
A method of correcting an error of an optical sensor which includes a light source and a detector, including adjusting a brightness of the light source to a preset brightness; controlling the light source to emit light to a preset material; acquiring preset material data corresponding to the emitted light and the preset material using the detector; and correcting, by using the acquired preset material data, an error of a distance between the light source and the detector based on a difference between a first amount of light received at a first point of the detector and a second amount of light received at a second point of the detector, or based on a gradation of an image obtained by the detector.

12 Claims, 22 Drawing Sheets

(56) References Cited

U.S. PATENT DOCUMENTS

| | | | | |
|---|---|---|---|---|
| 7,705,313 | B1 | 4/2010 | Russell | |
| 9,279,746 | B2 | 3/2016 | Wynn | |
| 9,763,558 | B2 | 9/2017 | Kobayashi et al. | |
| 10,578,547 | B2 | 3/2020 | Green et al. | |
| 10,609,349 | B2 | 3/2020 | Furuya | |
| 11,324,450 | B2 | 5/2022 | Joe et al. | |
| 11,382,572 | B2 | 7/2022 | Park et al. | |
| 11,536,814 | B2 | 12/2022 | Nakamura et al. | |
| 12,127,858 | B2 | 10/2024 | Park et al. | |
| 2007/0076189 | A1 | 4/2007 | Kumagai et al. | |
| 2008/0212436 | A1 | 9/2008 | Zijp et al. | |
| 2010/0045766 | A1 | 2/2010 | Imai et al. | |
| 2013/0258353 | A1 | 10/2013 | Kosmecki et al. | |
| 2018/0328855 | A1* | 11/2018 | Kido | G01N 21/8851 |
| 2019/0076099 | A1 | 3/2019 | Park et al. | |
| 2019/0090788 | A1* | 3/2019 | Nam | A61B 5/1455 |
| 2020/0018836 | A1 | 1/2020 | Nakamura et al. | |
| 2021/0239807 | A1 | 8/2021 | Ohki | |
| 2021/0259586 | A1* | 8/2021 | Oba | A61B 5/14532 |
| 2022/0287655 | A1 | 9/2022 | Park et al. | |
| 2023/0061628 | A1* | 3/2023 | Trittibach | A61B 3/0008 |

FOREIGN PATENT DOCUMENTS

| | | | | | |
|---|---|---|---|---|---|
| JP | 2010-271046 | A | 12/2010 | | |
| JP | 2015-008785 | A | 1/2015 | | |
| JP | 2016-102890 | A | 6/2016 | | |
| JP | 2016-142672 | A | 8/2016 | | |
| JP | 2018-155801 | A | 10/2018 | | |
| JP | 2020-008531 | A | 1/2020 | | |
| JP | 7516773 | B2 * | 7/2024 | ........ | A61B 5/14532 |
| KR | 10-2008-0032149 | A | 4/2008 | | |
| KR | 10-1607842 | B1 | 3/2016 | | |
| KR | 10-2017-0012658 | A | 2/2017 | | |
| KR | 10-2018-0072584 | A | 6/2018 | | |
| KR | 10-2018-0136661 | A | 12/2018 | | |
| KR | 10-2019-0029889 | A | 3/2019 | | |
| KR | 10-2020-0050835 | A | 5/2020 | | |
| KR | 10-2020-0055933 | A | 5/2020 | | |
| WO | 2020/084955 | A1 | 4/2020 | | |

OTHER PUBLICATIONS

Search Report (PCT/ISA/210) issued Jan. 6, 2022 by the International Searching Authority for International Patent Application No. PCT/KR2021/012886.

Written Opinion (PCT/ISA/237) issued Jan. 6, 2022 by the International Searching Authority for International Patent Application No. PCT/KR2021/012886.

Communication dated Jan. 7, 2026, issued by the Korean Ministry of Intellectual Property in Korean Application No. 10-2021-0124943.

* cited by examiner

PATH LENGTH [mm]

ABSORBANCE

METHOD AND APPARATUS FOR CORRECTING ERROR OF OPTICAL SENSOR, AND APPARATUS FOR ESTIMATING BIOMETRIC INFORMATION

CROSS-REFERENCE TO RELATED APPLICATIONS

This is a bypass continuation of International Application No. PCT/KR2021/012886, filed Sep. 17, 2021, which claims priority to Korean Patent Application No. 10-2020-0124753, filed on Sep. 25, 2020, and Korean Patent Application No. 10-2021-0124943, filed on Sep. 17, 2021, in the Korean Intellectual Property Office, the disclosures of which are incorporated by reference herein in their entireties.

BACKGROUND

1. Field

The disclosure relates to correcting an error of an optical sensor, and more particularly, to correcting an error of distance between a light source of an optical sensor and a detector.

2. Description of Related Art

Various types of biometric information may be estimated non-invasively using an optical sensor. In general, a spectrum may be measured from a sample to be analyzed through an optical sensor, and biometric information including antioxidant indicators may be estimated using absorbance of the measured spectrum. An optical sensor may be precisely designed to have a constant distance between a light source and a detector. When a distance between the optical sensor and the detector has an error of 0.1 mm, the absorbance may change by about 5%. Accordingly, in a case where there is a distance deviation between a light source and a detector for each device equipped with an optical sensor, the accuracy of an estimated biometric information value may be different from one device to another. In general, this error of distance may be corrected by measuring a physical distance between a light source of an optical sensor and a detector.

SUMMARY

Provided are an apparatus and method for correcting an error of an optical sensor using a difference in the amount of light between two points obtained from a preset material or the gradation of an image.

Additional aspects will be set forth in part in the description which follows and, in part, will be apparent from the description, or may be learned by practice of the presented embodiments.

In accordance with an aspect of the disclosure, a method of correcting an error of an optical sensor which includes a light source and a detector includes adjusting a brightness of the light source to a preset brightness; controlling the light source to emit light to a preset material; acquiring preset material data corresponding to the emitted light and the preset material using the detector; and correcting, by using the acquired preset material data, an error of a distance between the light source and the detector based on a difference between a first amount of light received at a first point of the detector and a second amount of light received at a second point of the detector, or based on a gradation of an image obtained by the detector.

The correcting of the error may further include: detecting a change in the distance between the light source and the detector with respect to a preset distance; and correcting the error of the distance between the light source and the detector based on the detected change in the distance.

The correcting of the error may further include: obtaining a slope corresponding to the first amount of light and the second amount of light; and detecting the change in the distance between the light source and the detector based on the obtained slope and a preset slope.

The correcting of the error may further include: obtaining a first slope between X-coordinate points corresponding to the first point and the second point, and a second slope between Y-coordinate points corresponding to the first point and the second point; and detecting the change in the distance between the light source and the detector based on the obtained first slope and the obtained second slope.

The correcting of the error may further include resetting coordinates of a detection area of the detector with respect to the light source based on the detected change in the distance between the light source and the detector.

The emitting of the light may further include emitting additional light from an additional light source, wherein the additional light has a same wavelength as the light emitted from the light source, and the correcting of the error may further include: detecting contour lines at positions corresponding to preset contour points from the preset material data; obtaining a contour slope between the detected contour lines; and detecting the change in the distance between the light source and the detector based on the obtained contour slope and a preset contour slope.

The correcting of the error may further include: detecting a vector between the light source and the additional light source, and moving coordinates of a detection area of the detector with respect to the light source along the detected vector based on the change in the distance between the light source and the detector.

In accordance with an aspect of the disclosure, an apparatus for correcting an error of an optical sensor comprising a light source and a detector includes at least one processor configured to: adjust a brightness of the light source to a preset brightness, drive the light source to emit light to a preset material, and correct, by using preset material data obtained by the detector, an error of a distance between the light source and the detector based on a difference between a first amount of light received at a first point of the detector and a second amount of light received at a second point of the detector, or based on a gradation of an image obtained by the detector.

The apparatus may further include a storage configured to store preset information including at least one of a preset brightness of a light source of a preset optical sensor, position information about preset points of the detector, a preset slope corresponding to the preset points, a preset contour slope corresponding to the preset points, and a preset distance between the light source and an image sensor.

The at least one processor may be further configured to: correct a change in the distance between the light source and the detector with respect to a preset distance, and correct the error of the distance between the light source and the detector based on the detected change in the distance.

The at least one processor may be further configured to: obtain a slope corresponding to the first amount of light and the second amount of light, and detect the change in the distance between the light source and the detector based on the obtained slope and a preset slope.

The at least one processor may be further configured to: obtain a first slope between X-coordinate points corresponding to the first point and the second point, and a second slope between Y-coordinate points corresponding to the first point and the second point, and detect the change in the distance between the light source and the detector based on the obtained first slope and the obtained second slope.

The at least one processor may be further configured to reset coordinates of a detection area of the detector with respect to the light source based on the detected change in the distance between the light source and the detector.

The at least one processor may be further configured to: drive an additional light source to emit additional light, wherein the additional light has a same wavelength as the light emitted from the light source, detect contour lines at positions corresponding to preset contour points from the preset material data, obtain a contour slope between the detected contour lines, and detect the change in the distance between the light source and the detector based on the obtained contour slope and a preset contour slope.

The at least one processor may be further configured to: detect a vector between the light source and the additional light source, and move coordinates of a detection area of the detector with respect to the light source along the detected vector based on the change in the distance between the light source and the detector.

In accordance with an aspect of the disclosure, a method of correcting an error of an optical sensor which includes a light source, a first detector, and a second detector, includes controlling the light source to emit light to a preset material; adjusting a brightness of the light source so that a measurement value of the first detector is same as a first measurement value; obtaining a second measurement value from the second detector; calculating a slope based on a difference between the first measurement value and the second measurement value; and correcting an error of a distance between the light source and the second detector based on the calculated slope.

The correcting of the error may further include obtaining a correction coefficient for the second measurement value based on the calculated slope.

The correcting of the error may further include: determining a length of an optical path between the light source and the second detector; and obtaining the correction coefficient for the second measurement value based on the determined length of the optical path.

The correcting of the error may further include: calculating the distance between the light source and the second detector based on the calculated slope; and determining the length of the optical path based on the calculated distance.

The correcting of the error may further include: calculating a ratio between a preset slope of a preset optical sensor and the calculated slope; and determining the length of the optical path based on the calculated ratio.

In accordance with an aspect of the disclosure, an apparatus for correcting an error of an optical sensor which includes a light source, a first detector, and a second detector, includes at least one processor configured to: control the light source to emit light to a preset material, adjust a brightness of the light source so that a measurement value of the first detector is same as a first measurement value, obtain a second measurement value from the second detector, calculate a slope based on a difference between the first measurement value and the second measurement value, and correct an error of a distance between the light source and the second detector based on the calculated slope.

In accordance with an aspect of the disclosure, an apparatus for estimating biometric information includes an optical sensor including a light source and a detector; and at least one processor configured to correct an error caused by a distance between the light source and the detector of the optical sensor, or caused by a state of the light source, using a preset material, and estimate biometric information using object data obtained using the optical sensor after the correcting, wherein to correct the error, the at least one processor may be further configured to: drive the light source to emit light to the preset material by adjusting a brightness of the light source to a preset brightness, and correct, by using preset material data obtained by the detector, the error of the distance between the light source and the detector of the optical sensor based on a difference between a first amount of light received at a first point of the detector and a second amount of light received at a second point of the detector, or based on an image gradation of an image obtained by the detector.

Based on a condition for correcting the state of the light source being satisfied, the at least one processor may be further configured to correct the state of the light source so that the brightness of the light source is same as the preset brightness.

Based on the error of the distance between the light source and the detector or the state of the light source being corrected, the at least one processor may be further configured to: correct a biometric information estimation model based on a correction result, and estimate biometric information using the corrected biometric information estimation model.

The at least one processor may be further configured to estimate biometric information using data acquired in a detection area reset as a result of error correction of the optical sensor.

The at least one processor may be further configured to estimate biometric information by applying a correction coefficient obtained as a result of error correction of the optical sensor to data obtained from an object.

BRIEF DESCRIPTION OF DRAWINGS

The above and other aspects, features, and advantages of certain embodiments of the present disclosure will be more apparent from the following description taken in conjunction with the accompanying drawings, in which.

DETAILED DESCRIPTION

Figure 1:
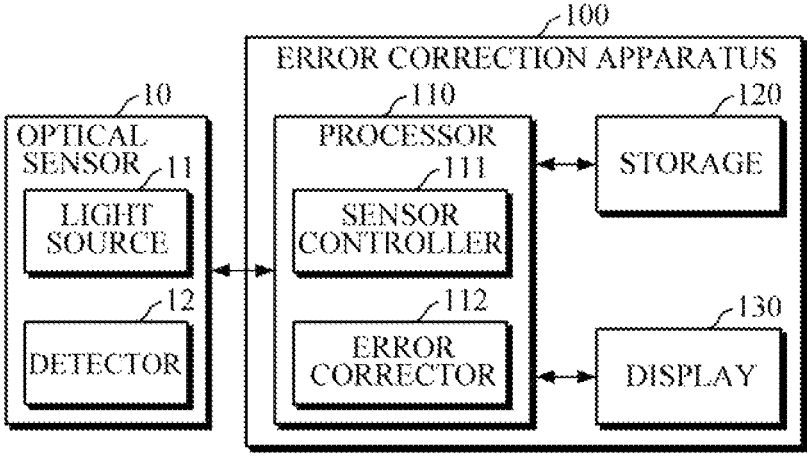
FIG. 1 is a block diagram illustrating an apparatus for correcting an error according to an embodiment.

Details of embodiments are included in detailed description and attached drawings. Features and advantages of the disclosure and methods for achieving them will be more clearly understood from detailed description of the following embodiments taken in conjunction with the accompanying drawings. Reference now should be made to the drawings, in which the same reference numerals are used throughout the different drawings to designate the same or similar components.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements and not the exclusion of any other elements. Terms such as "unit" and "module" denote units that process at least one function or operation, and they may be implemented by using hardware, software, or a combination of hardware and software.

Hereinafter, various embodiments of an apparatus and method for correcting an error of an optical sensor will be described in detail with reference to the drawings.

According to embodiments, an error of an optical sensor may be corrected using preset material data acquired through an optical sensor. In this way, accuracy of estimating biometric information including antioxidant indicators may be improved.

FIG. 1 is a block diagram illustrating an apparatus for correcting an error of an optical sensor according to an embodiment.

An optical sensor 10 may include a light source 11 and a detector 12. The light source 11 may be configured with one or more light emitting bodies, and may include, for example, a light emitting diode (LED), a laser diode (LD), and a phosphor, but embodiments are not limited thereto. The detector 12, which is a device configured to detect light and convert the light into an electric signal, may include a plurality of pixels that accumulate electric charge in response to light, sense a potential change due to the accumulated electric charge, and output a signal. In this case, the detector 12 may be a complementary metal-oxide semiconductor (CMOS) image sensor, a photodiode array, or one or more photodiodes, but embodiments are not limited thereto.

The optical sensor 10 may be mounted in devices that estimate various types of biometric information including antioxidant indicators. The light source 11 and the detector 12 of the optical sensor 10 may be arranged in various shapes and may have a constant preset distance between each other depending on the size of the form factor of the devices, a measurement site of an object, the type of biometric information to be analyzed, or the like. However, at the time of manufacturing the optical sensor 10, a distance between the light source 11 and the detector 12 may slightly deviate from a standard or preset distance, which may reduce the accuracy of a signal measured by the optical sensor 10. An error correction apparatus 100 for correcting an error of the optical sensor 10 may correct the distance deviation between the light source 11 and the detector 12.

Referring to FIG. 1, the error correction apparatus 100 may include a processor 110, a storage 120, and a display 130. The processor 110, the storage 120, and the display 130 of the error correction apparatus 100 may be integrated into one hardware component, or may be separately implemented in two or more different hardware components.

The processor 110 may include a sensor controller 111 which may be connected directly or through wireless communication to the optical sensor 10 to be corrected and configured to control the driving of the optical sensor 10, and an error corrector 112 which is configured to correct an error of the optical sensor 10 by using a signal output from the optical sensor 10.

The sensor controller 111 may drive the light source 11 to be corrected of to emit light to a preset material. Here, the preset material may be a reflective mirror that reflects the light of the light source, or a reflector with a reflective material applied on a front surface thereof. The reflective material may be a diffuse reflection material having a reflectance of 1% to 99T, and may include, for example, barium sulfate (BaSo4), Teflon (PTEF), etc., but embodiments are not limited thereto. However, the preset material is not limited thereto, and may be pure water or a solution, a solid material, or a semisolid material that replicates the components of the object.

In order to prevent an optical path from being changed according to the brightness of the light source 11 when the light source 11 is driven, the sensor controller 111 may acquire preset brightness information of a preset optical sensor that corresponds to the light source 11 by referring to preset brightness information stored in the storage 120, and adjust the brightness of the light source 11 to the preset brightness. In this case, the preset brightness information stored in the storage 120 may include a preset or standard current intensity, a preset or standard duration, a preset or standard amount of light, and the like. For example, a light source to be corrected may be driven at a preset current intensity by the sensor controller 111. In another example, the sensor controller 111 may control the current intensity of the light source 11 to be driven so that the amount of light measured at a preset point by the detector 12 is the same as a preset amount of light measured at a preset point by a preset optical sensor detector. In this case, the sensor controller 111 may output an error message through the display 130 when the brightness of the light source 11 to be corrected cannot be adjusted to the preset brightness.

When data is generated as the light emitted by the light source 11 to be corrected is reflected by the preset material and the reflected light is detected by the detector 12, the error corrector 112 may receive preset material data from the detector 2 and correct an error of distance between the light source 11 and the detector 12 by using the received preset material data. For example, the error corrector 112 may use the gradation of the preset material image to compute the degree of change in the distance between the light source 11 and the detector 12 compared to the preset distance between the light source of the preset optical sensor and the detector. The error corrector 112 may reset coordinates of a detection area of the detector 12 with respect to the light source 11, or determine a correction coefficient for correcting a measurement value measured by the detector 12, for example, wavelength-specific absorbance, based on the computed degree of change in the distance between the light source 11 and the detector 12.

The storage 120 may store preset information necessary for error correction. For example, the preset information may include preset brightness information of a light source of a preset optical sensor, for example, a preset or standard amount of light, a preset or standard current intensity, and/or a preset or standard duration. In addition, the preset information may include position information of preset points on the detector of the preset optical sensor (e.g., pixel coordinates of preset points), a preset slope between preset points, a preset contour position, a preset contour slope between preset contour lines and/or a preset distance between the light source and the detector of the preset optical sensor, and the like. However, the preset information is not limited to the above examples.

The storage 120 may include a storage medium, such as a flash memory type, a hard disk type, a multimedia card micro type, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like, but embodiments are not limited thereto.

The display 130 may visually provide information processed by the processor 110. The display 130 may visually display the image gradation of the preset material, a position of a detection area of the detector prior to error correction of the light source, and/or a position of a detection area of the detector reset after error correction, or the coordinate axis before and after correction. The display 230 may include a display, a hologram device, or a projector, and include a touch circuitry set to sense a touch and/or a sensor circuitry set to measure a magnitude of a force generated by a touch, for example, a pressure sensor, or the like.

Hereinafter, example embodiments in which the error correction apparatus 100 corrects an error of an optical sensor 10 including a plurality of LEDs 310 and an image sensor 320 are described below with reference to FIGS. 2 to 7C. However, embodiments are not limited thereto, and may be applicable to an optical sensor including another type of light source and/or a photodiode array.

Figure 2:
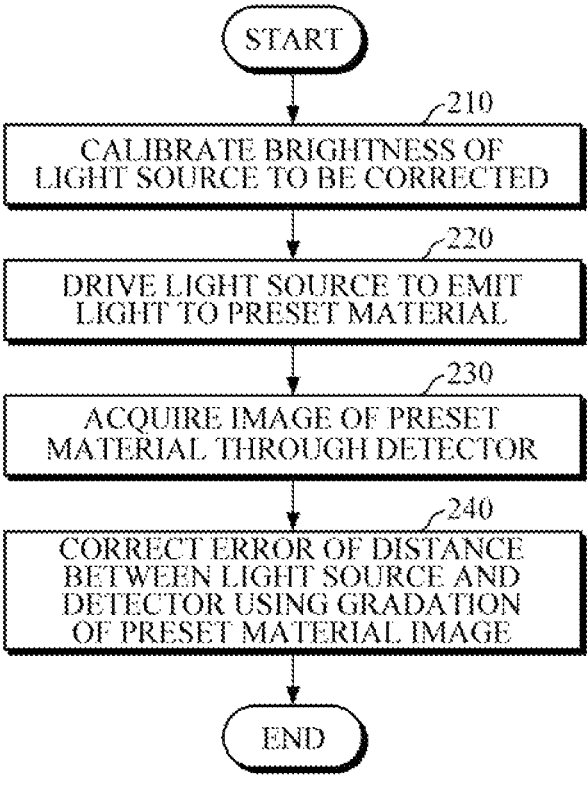
FIG. 2 is a flowchart illustrating a method of correcting an error according to an embodiment.
Figure 3A:
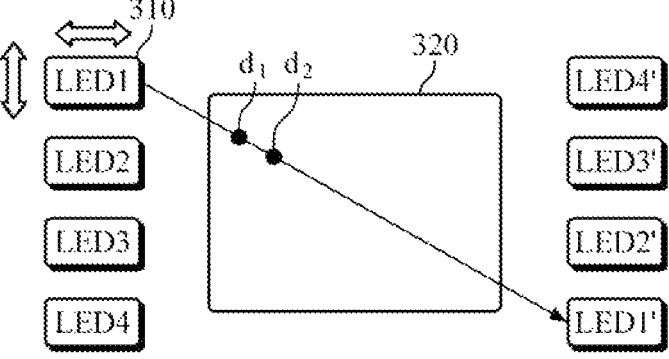
FIGS. 3A and 3B are diagrams for describing examples correcting an error of an optical sensor, according to embodiments.
Figure 3B:
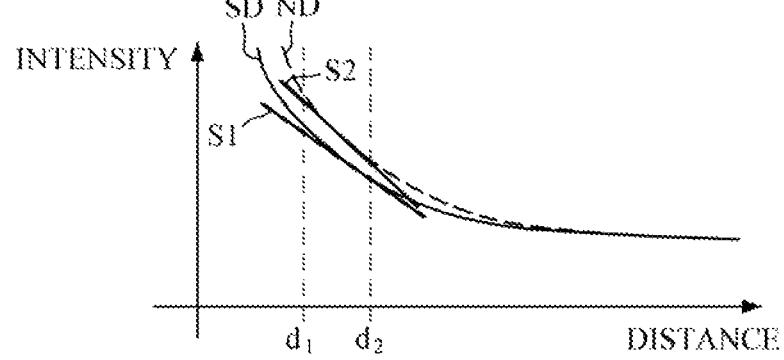

FIG. 2 is a flowchart illustrating a method of correcting an error according to one embodiment. FIGS. 3A and 3B are diagrams for describing an embodiment of correcting an error of an optical sensor.

Referring to FIG. 2, at operation 210 the sensor controller 111 may select a light source to be corrected and calibrate the brightness of the selected light source.

Referring to FIG. 3A, an optical sensor may include an image sensor 320 disposed at the center thereof and a plurality of LEDs 310 disposed around the image sensor 320. In this case, the LEDs may be arranged around the image sensor 320 in a predetermined shape. For example, as illustrated in FIG. 3A, a first plurality of LEDs, for example LED1, LED2, LED3, and LED4, may be disposed on one side of the image sensor 320 and a second plurality of LEDs, for example LED1', LED2', LED3', and LED4', may be disposed on the other side of the image sensor 320. In this case, each LED of the first plurality of LEDs may emit light of different wavelengths from each other, and each LED of the second plurality of LEDs may emit light of different wavelengths from each other. In embodiments, each LED of the first plurality of LEDs may emit light of a same wavelength as a corresponding LED of the second plurality of LEDs. For example, LED1 and LED1' may emit light of a first wavelength, LED2 and LED2' may emit light of a second wavelength, LED3 and LED3' may emit light of a third wavelength, and LED4 and LED4' may emit light of a fourth wavelength. Each LED 310 may be disposed at a preset or standard distance from the image sensor 320, that is, at a distance corresponding to the distance between the LED of the preset optical sensor and the image sensor. However, the distance between each LED and the image sensor 320 may slightly deviate from the preset or standard distance due to various factors in manufacturing.

The sensor controller 111 may select an LED to be corrected, for example, LED1, in order to correct an error due to a slight change in distance between the light source 310 and the image sensor 320, and adjust the brightness of the selected LED1 to the preset brightness of LED1 of the preset optical sensor in a state where the selected LED1 is set to have the same optical path as the LED1 of the preset optical sensor.

Then, at operation 220 the sensor controller 111 may drive the LED 310, which has been calibrated to the present brightness, to emit light to a preset material.

Then, based on preset material data being obtained through the image sensor 320 at operation 230, the error corrector 112 at operation 240 may use the obtained preset material data to correct the error of distance between the driven LED and the image sensor using a difference in the amount of light between at least two points or a gradation of an image. Image data of the preset material obtained by the image sensor 320 may include, for example, data on the amount of light received by each pixel of the image sensor 320, and the amount of light of each pixel may be represented as an image gradation of the preset material.

When the optical sensor is manufactured, a slight change in the position of the LED 310 is a factor that may cause a change in the gradation of the preset material image obtained by the image sensor 320. For example, as shown in FIGS. 3A and 3B, a slope 51 and S2 between two points d1 and d2 of the image sensor may be different between the preset optical sensor SD and the optical sensor ND to be corrected.

Therefore, the error corrector 112 may calculate a slope between preset points on the image sensor 320 which are designated for each LED 310, and detect a change in distance between the light source and the image sensor by comparing the calculated slope with a preset slope between the preset points of the preset optical sensor.

Equations 1-5 below are example equations for calculating a change in distance between a light source and an image sensor using a slope between preset points and a calculated slope.

$$G_{L1} = \frac{I(d_1) - I(d_2)}{d_1 - d_2} \qquad \text{Equation 1}$$

9

-continued $$G'_{L1} = \frac{I(d'_1) - I(d'_2)}{d'_1 - d'_2}$$        Equation 2

$$d'_1 = d_1 + \Delta$$        Equation 3

$$d'_2 = d_2 + \Delta$$        Equation 4

$$\Delta = \frac{1}{\mu}\ln\left(\frac{G}{G1}\right)$$        Equation 5

Here, $d_1$ and $d_2$ denote standard distances from a light source of a preset optical sensor to preset points of an image sensor, for example, pixel coordinates $(x_1, y_1)$ and $(x_2, y_2)$. The preset points may be set for each LED of the light source. In addition, d'1 and d'2 denote distances from a light source of an optical sensor to be corrected to preset points of an image sensor, for example, pixel coordinates $(x_1, y_1)$ and $(x_2, y_2)$. That is, a preset point position is the same pixel position on the image sensor of the preset optical sensor and on the image sensor of the optical sensor to be corrected, and a distance from a position of an LED to each preset point is changed according to the change in the position of the LED. Further, $G_{L1}$ and $G'_{L1}$ denote slopes between preset points of the preset optical sensor and between preset points of the optical sensor to be corrected, respectively. Also, $I(d_1)$ and $I(d_2)$ each denote an intensity of light received at a preset point position of the preset optical sensor or an absorbance at the preset point position, and $I(d'_1)$ and $I(d'_2)$ each denote an intensity of light received at a preset point position of the optical sensor to be corrected or an absorbance at the preset point position. $\mu$ denotes an absorption coefficient pre-acquired for a preset material. Here, the absorbance may be obtained by the Lambert-Beer's law.

The error corrector 112 may sequentially calculate a change A in distance between each LED and the image sensor for all LEDs of the light source of the optical sensor to be corrected compared to the preset optical sensor, and adjust a detection area of the image sensor for each LED. For example, the coordinate axis of the image sensor may be reset by being moved by a distance corresponding to the distance change A, or the detection area set in the image sensor for each LED may be moved.

Figure 4:
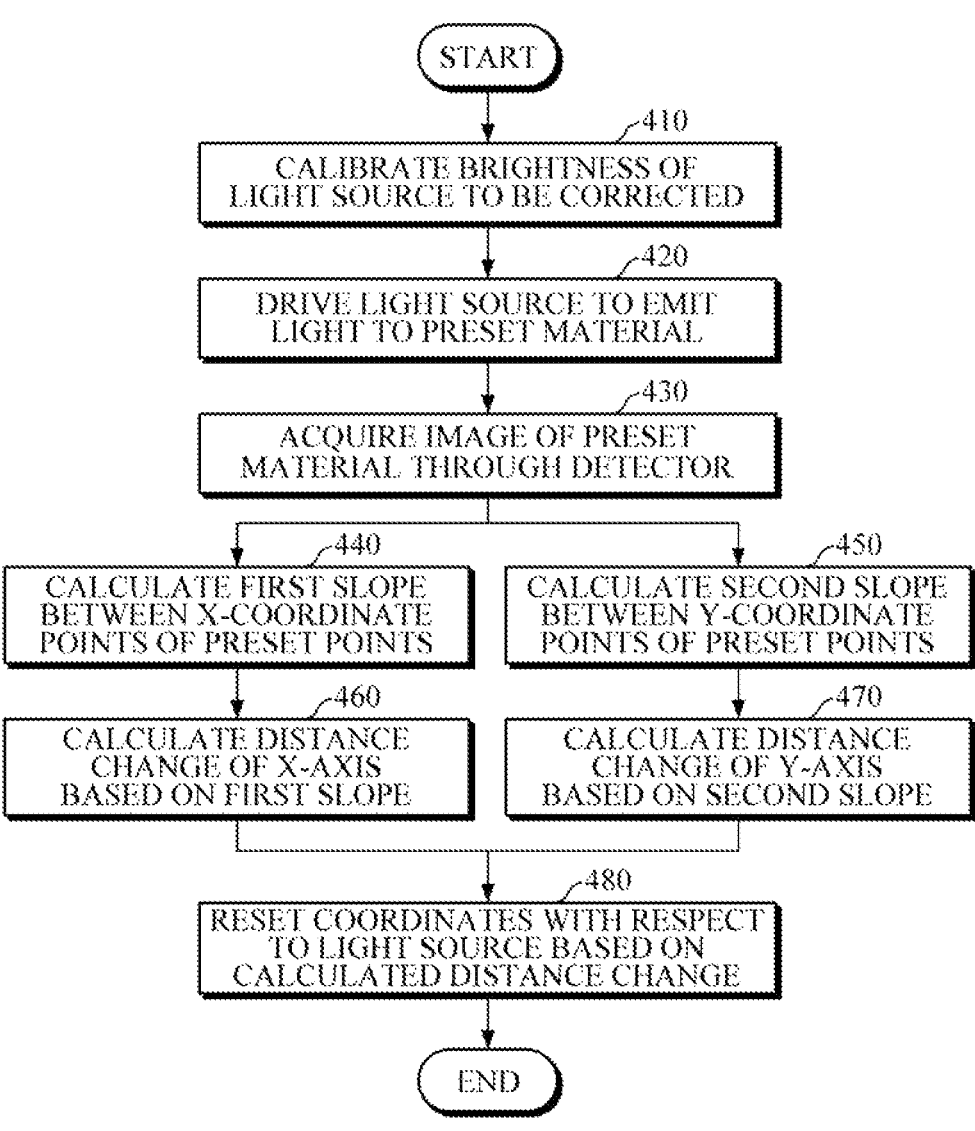
FIG. 4 is a flowchart illustrating a method of correcting an error according to an embodiment.
Figure 5A:
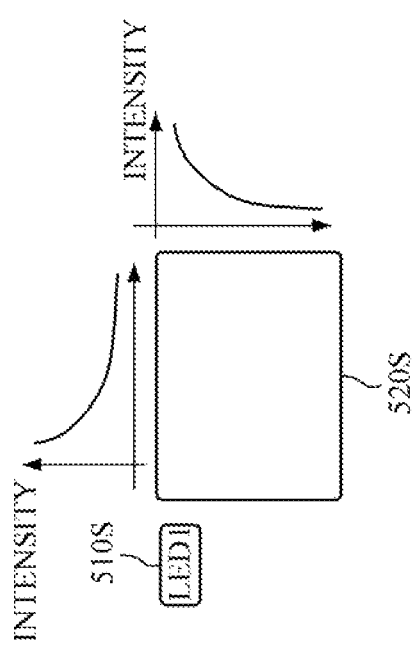
FIGS. 5A to 5C are diagrams for describing an example of correcting an error of an optical sensor according to an embodiment.
Figure 5A:
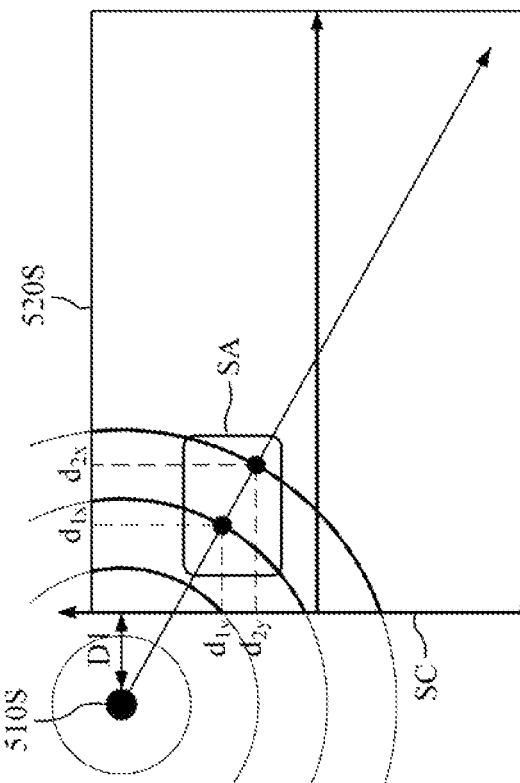
Figure 5B:
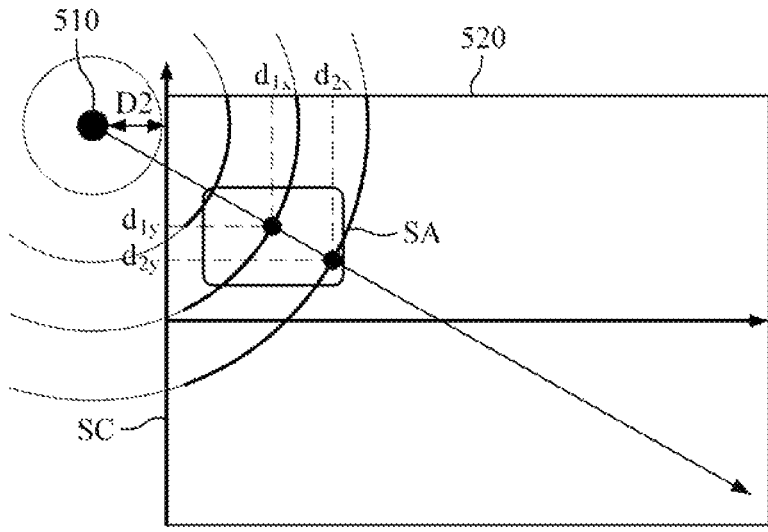
Figure 5C:
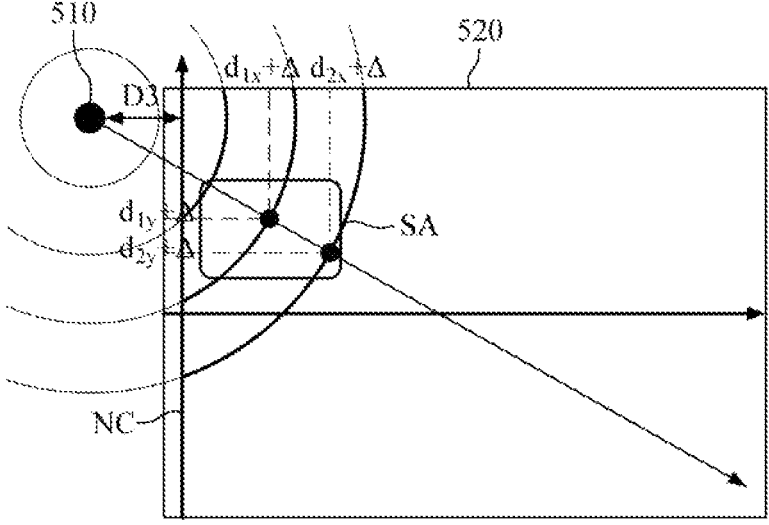

FIG. 4 is a flowchart illustrating a method of correcting an error according to another embodiment. FIGS. 5A to 5C are diagrams for describing an embodiment of correcting an error of an optical sensor.

Referring to FIG. 4, at operation 410 the sensor controller 111 may adjust the brightness of a light source to be corrected to a preset brightness of a light source of a preset optical sensor, and at operation 420 the light source is driven to emit light to a preset material. Then, at operation 430 preset material data may be obtained by a detector (430).

Then, at operation 440 the error corrector 112 may calculate a first slope between X-coordinate points of preset points using a gradation of the preset material data, and at operation 450 the error corrector 112 may calculate a second slope between Y-coordinate points of the preset points FIG. 5A illustrates a preset optical sensor, in which LED1 of the preset optical sensor is disposed at a position 510S apart from a coordinate axis SC of an image sensor 520S by a preset distance D1. FIG. 5B illustrates an optical sensor to be corrected, in which LED1 is further shifted toward the image sensor 520 compared to the preset optical sensor and is disposed apart at a position 510 by a distance D2. As shown in FIG. 5A, assuming that a preset detection area SA for the LED1 at position 510S of the preset optical sensor is set around the preset point positions $(d_{1x}, d_{1y})$ and $(d_{2x}, d_{2y})$, the preset detection area SA must also be shifted as the position of the LED1 at position LED 510 of the optical sensor to be corrected is shifted, in order to measure a constant signal from the same preset material through the same LED1.

In this way, in order to appropriately shift the detection area SA of the image sensor for each light source according to the change in the position of the light source, the error corrector 112 may individually calculate the first slope on the X-axis and the second slope on the Y axis through Equations 1-5 described above based on, respectively, the change in the light intensity of the X-coordinate points d1$x$ and d2$x$ at the preset point positions and the change in the light intensity of the Y-coordinate points $d_{1y}$ and $d_{2y}$ at the preset point positions.

Then, at operation 460 and operation 470, the error corrector 112 may separately calculate the distance change of the X-axis and the distance change of the Y-axis through Equations 1-5 above by using the first slope and the second slope individually calculated for the X- and Y-axes.

Then, at operation 480 the coordinate axis may be reset based on the distance change of the X-axis and the distance change of the Y-axis. FIG. 5C illustrates that a coordinate axis NC may be reset with respect to LED1 at position 510, which is to be corrected, wherein the new coordinate axis NC may be reset so that a distance between the LED1 at position 510 and the new coordinate axis of the image sensor 520 is the same as a preset distance D1 or becomes a distance D3 within a predetermined threshold.

Figure 6:
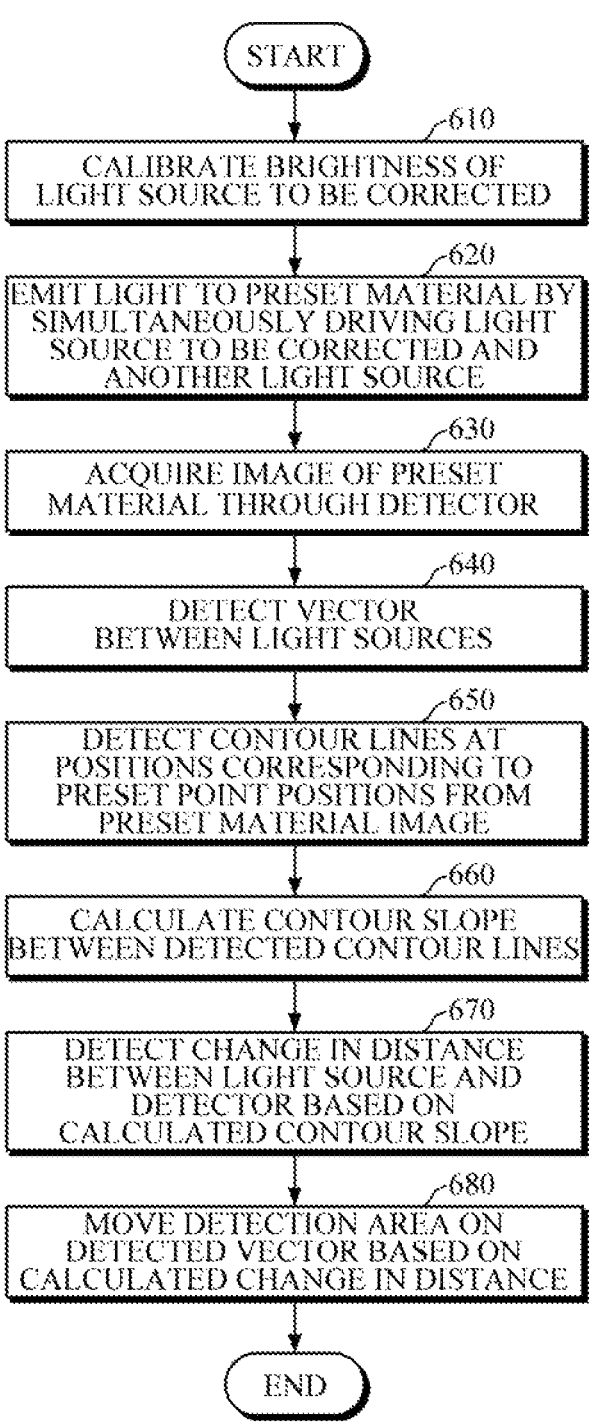
FIG. 6 is a flowchart illustrating a method of correcting an error according to an embodiment.

FIG. 6 is a flowchart illustrating a method of correcting an error according to another embodiment. FIGS. 7A to 7D are diagrams for describing an embodiment of correcting an error of an optical sensor.

Referring to FIG. 6, at operation 610 the sensor controller 111 may adjust a brightness of a first light source to be corrected to a preset brightness of a light source of a preset optical sensor, and at operation 620 a first light source may be driven to emit light to a preset material. In this case, the sensor controller 111 may simultaneously drive the first light source to be corrected and a second light source. Here, the second light source may be disposed at a position facing the first light source with respect to the image sensor. Also, the second light source may emit light of the same wavelength as the first light source.

Then, based on the image sensor acquiring preset material image data at operation 630, the error corrector 112 at operation 640 may detect a vector between the first light source and the second light source. In this case, the vector may be detected based on the arrangement positions of the first light source and the second light source.

Figure 7A:
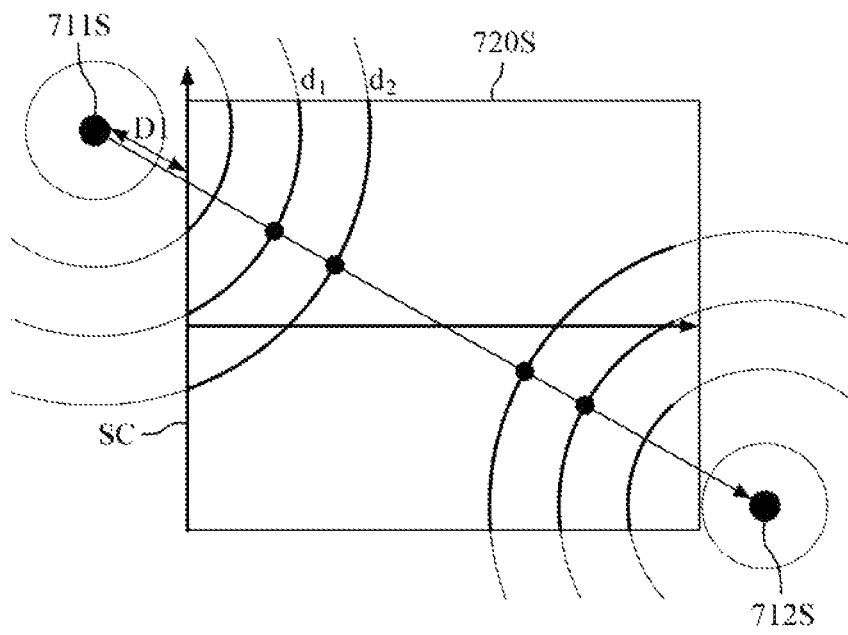
FIGS. 7A to 7D are diagrams for describing an example of correcting an error of an optical sensor, according to an embodiment.
Figure 7B:
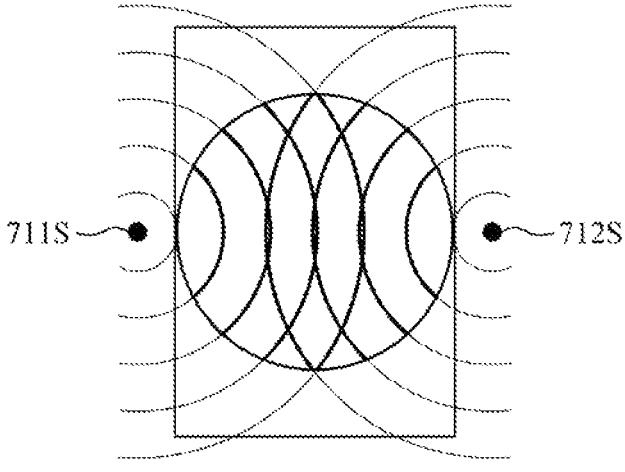
Figure 7C:
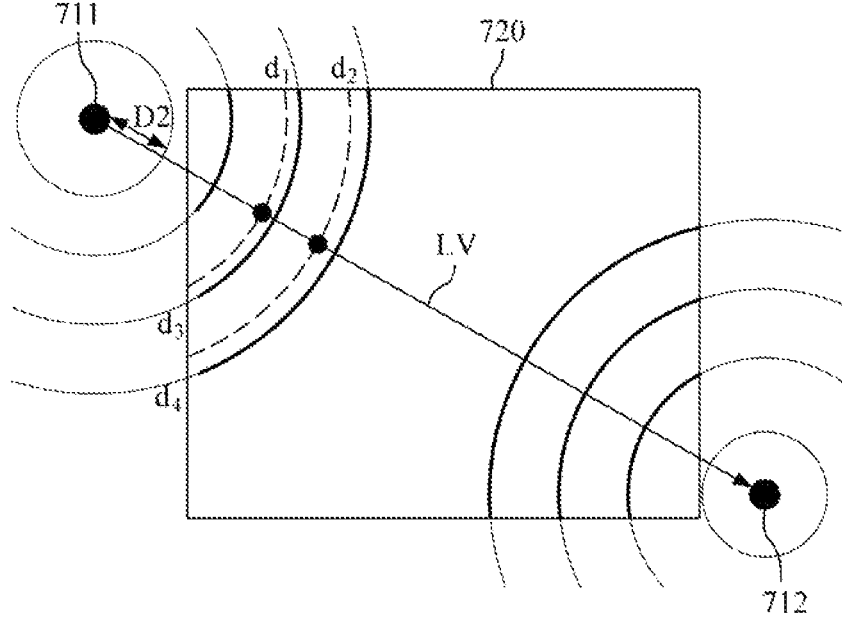

Then, at operation 650, contour lines at positions corresponding to preset point contour positions may be detected from the preset material image data acquired in operation 630. For example, FIGS. 7A and 7B illustrates that a first LED at position 711S of the preset optical sensor and a second LED at position 712S positioned opposite to the first LED at position 711S across an image sensor 720S are driven. In this way, by driving the light sources at position 711S and position 712S positioned opposite to each other, contour lines can be more clearly generated on the image. Referring to FIGS. 7A and 7B, preset contour lines d1 and d2 at the time when the first LED at position 711S of the preset optical sensor is apart from a coordinate axis of an image sensor 720 by a preset distance D1, and a preset contour slope between the preset contour lines d1 and d2 may be preset. FIG. 7C illustrates that a first LED 711 of an optical sensor to be corrected is shifted toward the image sensor 720 compared to the preset optical sensor and is apart from the image sensor 720 by a distance D2. The error corrector 112 may detect the contour lines (d1 and d2 of FIG. 7C) at positions corresponding to the preset contour lines (d1 and d2 of FIG. 7A) from the preset material image acquired in operation 630.

Then, a contour slope between the detected contour lines (d1 and d2 of FIG. 7C) may be calculated at operation 660. For example, a slope between intersections between the contour lines (d1 and d2 of FIG. 7C) and the vector detected in operation 640 may be calculated as the contour slope through Equation 1. However, embodiments are not limited thereto, and various known methods of detecting contour lines from an image and detecting a slope between contour lines may be used.

Then, at operation 670 a change in the distance between the light source and the image sensor may be detected based on the calculated contour slope. For example, a distance change may be detected by comparing the preset contour slope between the preset contour lines calculated through the preset optical sensor and the contour slope calculated in operation 650.

Figure 7D:
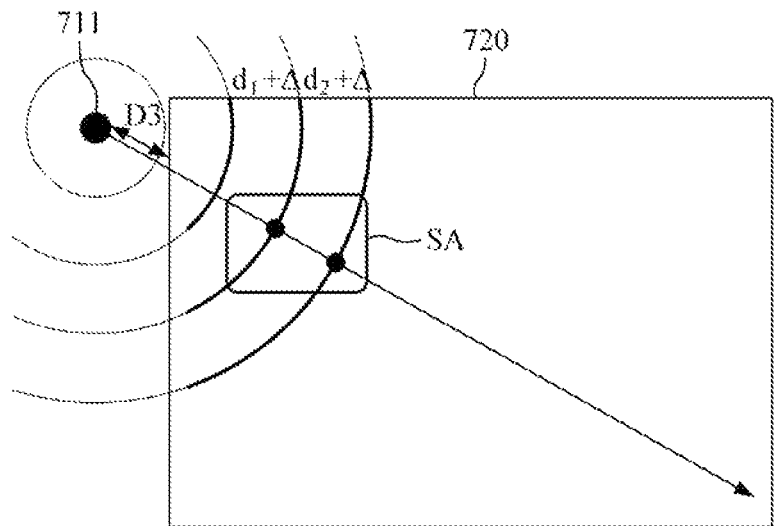

Then, at operation 680 a detection area or the coordinate axis may be moved in a direction of the vector detected in operation 640 based on the calculated distance change. FIG. 7D illustrates that a detection area SA for the first LED 711 is moved.

Figure 8:
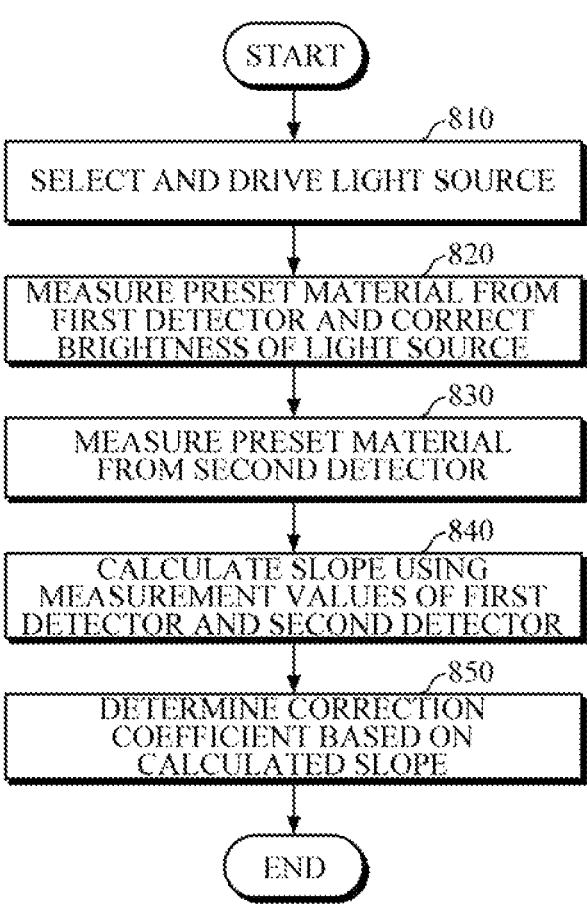
FIG. 8 is a flowchart illustrating a method of correcting an error according to an embodiment.
Figure 9A:
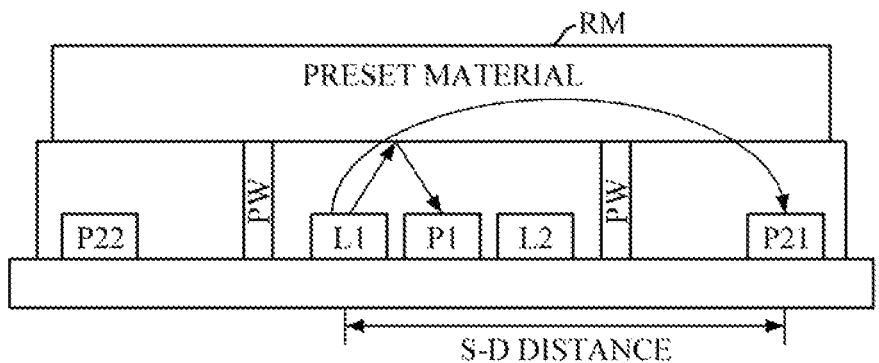
FIGS. 9A to 9C are diagrams for describing an example of correcting an error of an optical sensor, according to an embodiment.
Figure 9B:
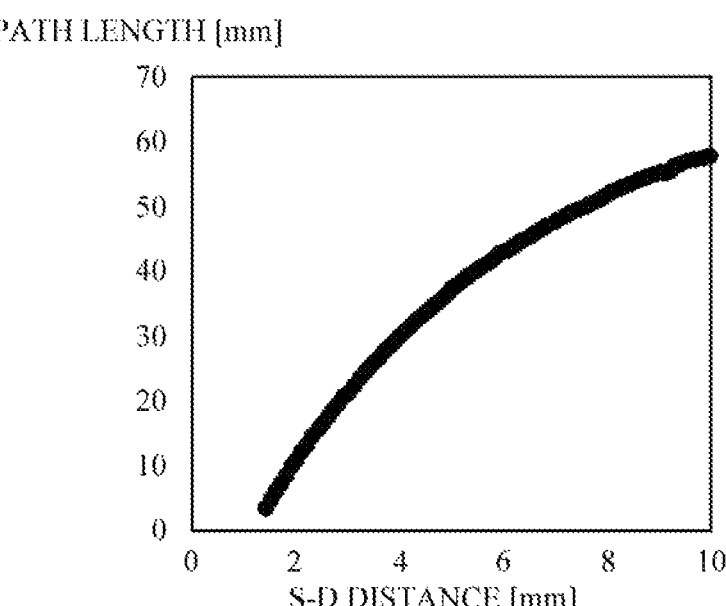
Figure 9C:
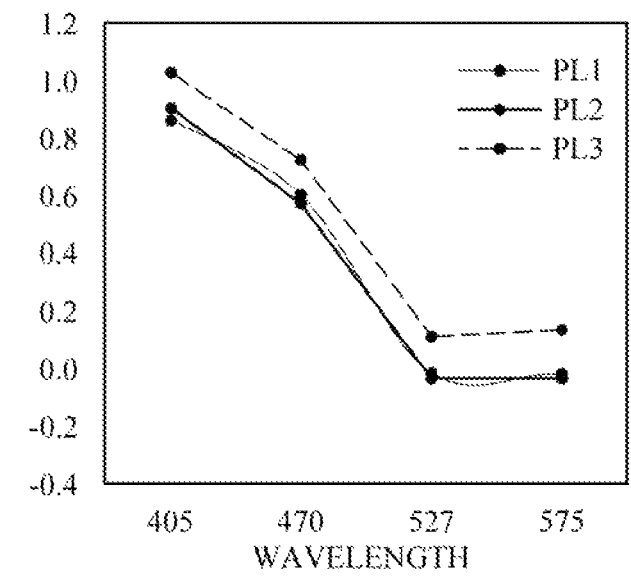

FIG. 8 is a flowchart illustrating a method of correcting an error according to another embodiment. FIG. 9A is a cross-sectional view illustrating an optical sensor including one or more LEDs and a plurality of photodiodes, and FIGS. 9B and 9C are diagrams for describing an example embodiment of correcting an error of the optical sensor.

As shown in FIG. 9A, an optical sensor may have partition walls PW positioned on both side surfaces thereof and one or more photodiodes P1 for monitoring states of one or more LEDs L1 and L2 and light sources L1 and L2 may be disposed between the partition walls PW. In addition, one or more photodiodes P21 and P22 to be used when estimating biometric information may be disposed outside the partition walls PW. Hereinafter, correction of error of the optical sensor to be described below may be performed for all light sources L1 and L2 and all photodiodes P21 and P22.

According to one example embodiment, a plurality of LEDs, partition walls, and photodiodes for estimating biometric information may be concentrically arranged around the photodiode P1 for monitoring the states of the light sources.

First, at operation 810 a sensor controller 111 may select and drive the LED L1 to be corrected, and at operation 820 the sensor controller 111 may adjust the brightness of the selected LED L1 to a preset brightness.

For example, the sensor controller 111 may drive, for example, the LED L1 to be corrected, and adjust the brightness of the LED L1 to be corrected to the preset brightness by using a measurement value of, for example, a first photodiode P1. For example, current intensity may be adjusted so that the amount of light measured by the first photodiode P1 is the same as a preset amount of light of a preset optical sensor.

Then, at operation 830 a preset material RM may be measured through, for example, a second photodiode P21 in a state where the brightness of the LED L1 is the same as the preset brightness.

Then, at operation 840 the error corrector 112 may calculate a slope using a first measurement value of the first photodiode P1 measured when the brightness of the LED L1 becomes the preset brightness, that is, the preset amount of light and a second measurement value of the second photodiode P21.

For example, as shown in Equation 6 below, the slope may be calculated based on a difference between the first measurement value and the second measurement value.

$$S_m = \frac{I_2 - I_1}{d_{ref}} \qquad \text{Equation 6}$$

Here, $S_m$ denotes a slope to be calculated. $I_1$ denotes the first measurement value of the first photodiode P1, $I_2$ denotes the second measurement value of the second photodiode P21, and $d_{ref}$ is a preset distance between an LED and a photodiode of the preset optical sensor.

Then, at operation 850 the error corrector 112 may correct an error of distance between the LED L1 and the second photodiode P21 based on the calculated slope. For example, a correction coefficient for correcting an error of the second measurement value according to the change in distance between the LED L1 of the optical sensor to be corrected and the second photodiode PD21 compared to the preset distance of the preset optical sensor may be obtained.

For example, the error corrector 112 may calculate a distance between the LED L1 and the second photodiode PD21 through Equation 7 below, determine a length of an optical path between the LED L1 and the second photodiode PD21 based on the degree of change in the calculated distance compared to the preset distance, and obtain a correction coefficient based on the degree of change in the determined length of the optical path compared to a preset optical path length of the preset optical sensor.

$$d_{new} = -\frac{1}{\varepsilon c} \log\left(\frac{d_{ref} \times S_m}{const} + 1\right) \qquad \text{Equation 7}$$

Here, $d_{new}$ denotes the distance between the LED L1 and the second photodiode PD21, and $\varepsilon$ and c denote a molar absorption coefficient and concentration with respect to the preset material, respectively, and are preset values. $d_{ref}$ denotes the preset distance of the preset optical sensor, const denotes the preset amount of light of the preset optical sensor, and $S_m$ denotes the calculated slope.

FIG. 9B illustrates an example showing a relationship between a distance between a light source and a detector and a length of optical path, and an optical path length determination model that represents the relationship between a distance between a light source and a detector and the length of optical path may be predefined as an equation or a lookup table. The error corrector 112 may determine the length of optical path using the optical path length determination model.

FIG. 9C illustrates an example showing a change in wavelength-specific absorbance according to different optical path lengths PL1, PL2, and PL3. A correction coefficient acquisition model that represents the relationship between the degree of change in the optical path length and an absorbance correction coefficient may be predefined in the form of an equation or a lookup table by analyzing the degree of change in the optical path length compared to the preset optical path length and the degree of change in the wavelength-specific absorbance. The error corrector 112 may obtain the correction coefficient using the correction coefficient acquisition model.

In another example, the error corrector 112 may obtain a ratio Sm/Sref between the calculated slope Sm and the preset slope Sref of the preset optical sensor and determine the degree of change in the distance of the optical sensor to be corrected. In this case, a distance variation acquisition model that represents the relationship between the slope ratio and the degree of change in the distance may be predefined in the form of an equation or a lookup table, and the degree of change in the distance may be obtained using the distance variation acquisition model. When the degree of change in the distance is obtained, the error corrector 112 may determine a length of the optical path between the LED L1 and the second photodiode PD21 as described above, and obtain the correction coefficient based on the determined degree of change in the distance of optical path compared to the preset optical path length.

Figure 10:
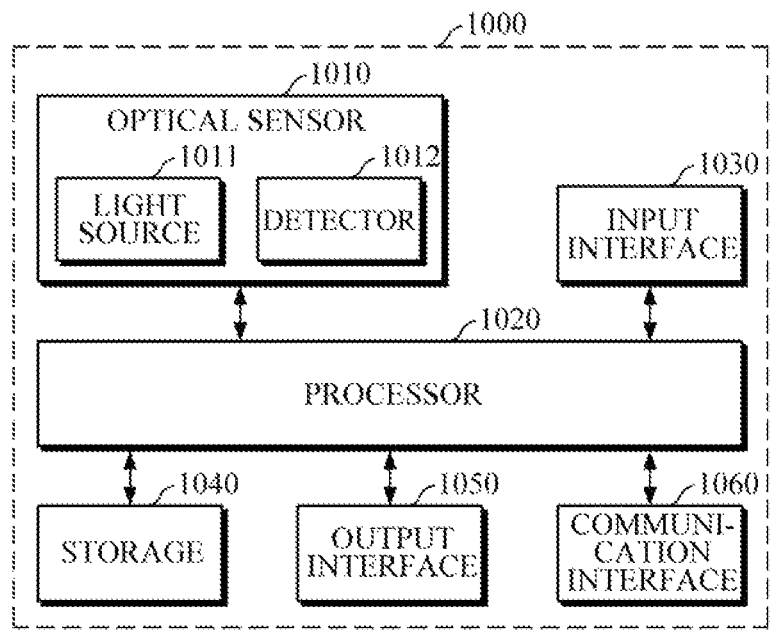
FIG. 10 is a diagram illustrating an apparatus for estimating biometric information according to an embodiment.

FIG. 10 is a diagram illustrating an apparatus for estimating biometric information according to an example embodiment.

Referring to FIG. 10, an apparatus 1000 for estimating biometric information may include an optical sensor 1010, a processor 1020, an input interface 1030, a storage 1040, an output interface 1050, and a communication interface 1060. Each component may be integrated into one hardware component, or may be distributed on two or more physically separate hardware components.

The optical sensor 1010 may include a light source 1011 and a detector 1012. When light is scattered or reflected by an object irradiated by light emitted from the light source 1011, the optical sensor 1010 may detect the scattered or reflected light through the detector 1012 and acquire spectrum data of the light or a biometric signal, such as a pulse wave signal. The light source 1011 may include one or more light emitting bodies, such as LEDs, LDs, or the like, and each light emitting body may be configured to have a different wavelength. The detector 1012 may be a CMOS image sensor, one or more photodiodes, or a photodiode array, but embodiments are not limited thereto.

The processor 1020 may be connected to each of the optical sensor 1010, the input interface 1030, the storage 1040, the output interface 1050, and the communication interface 1060 of the apparatus 1000, generate a control command to control each component, and transmit the control command to each component. The processor 1020 may also receive data from each component and process the received data. The processed data may also be transmitted to other components so that necessary operations can be performed by the other components.

The processor 1020 may correct an error of a distance between the light source 1011 and the detector 1012 of the optical sensor 1010 using a preset material prior to using the apparatus 1000, for example, at the time of manufacturing the apparatus 1000, or at the time of initially using the apparatus 1000 by a user.

The processor 1020 may adjust a brightness of the light source 1011 to be corrected on the basis of preset brightness information of a preset optical sensor, and correct an error of a distance between the light source 1011 and the detector 1012 based on a difference in the amount of light between at least two points or an image gradation by using measurement data of the detector 1012. For example, the light source 1011 may be driven at a preset current intensity of the preset brightness information, or the brightness of the light source 1011 may be adjusted by adjusting the current intensity of the light source 1011 so that the amount of light measured at a preset point of the detector 1012 is the same as a preset amount of light of the preset brightness information. In this case, the preset point of the detector may refer to a pixel at a predetermined position among a plurality of pixels when the detector is an image sensor or a photodiode array, and may refer to a predefined monitoring detector when there are a plurality of detectors. An error message may be output using the output interface 1050 when the brightness of the light source 1011 cannot be adjusted to the preset brightness. Example embodiments of error correction are described in detail above and thus are not described hereinafter.

In addition, when the apparatus 1000 is used, the state of the light source, such as the brightness of the light source, may change. Thus, each time conditions for correcting the light source state, such as user request, a preset period, environmental changes (e.g., temperature, humidity, etc.), correctable state (e.g., when the optical sensor is in contact with the preset material), and the like, are satisfied, the processor 1020 may correct the state of the light source 1011 using the preset material so that the brightness of the light source 1011 becomes the preset brightness. In embodiments, an error message may be output using the output interface 1050 when the brightness of the light source 1011 cannot be adjusted to the preset brightness.

For example, the processor 1020 may adjust the current intensity of the light source 1011 so that the amount of light measured at a preset point of the detector 1012, for example, a pixel at a predetermined position when the detector is an image sensor or a photodiode array, or the amount of light measured by a predefined monitoring detector when there are a plurality of detectors, is the same as the preset amount of light. The adjusted current intensity may be stored in the storage 1040 as a preset current intensity for the corresponding light source 1011.

In embodiments, the processor 1020 may guide the user using the output interface 1050 to position the apparatus 1000 on the preset material when the condition for correcting the light source state is satisfied.

For example, the preset material may be a charger that supplies power to the apparatus 1000, and a reflective material may be disposed or applied at a position where the optical sensor 1010 is in contact with the charger or faces the optical sensor 1010 when the apparatus 1000 is placed on the charger. The processor 1020 may visually or acoustically guide the user to place the main body of the apparatus 1000 on the charger through the output interface 850.

Upon receiving a request for estimating biometric information, the processor 1020 may control the optical sensor 1010 using a correction result of the light source state, for example, the current intensity of the adjusted light source, to obtain wavelength-specific absorbance data from the object, and estimate biometric information using an error of distance of the optical sensor 1010 and/or the correction result of the light source state, and/or the biometric information estimation model. In this case, the biometric information may include antioxidant materials, such as carotenoids, blood glucose, urea, uric acid, lactate, triglyceride, calorie, protein, cholesterol, moisture, chromophore, ethanol, blood pressure, vascular age, arterial stiffness, aortic pressure waveform, blood vessel elasticity, stress index, a degree of fatigue, skin age, and skin elasticity, but embodiments are not limited thereto.

For example, the processor 1020 may estimate the biometric information using the wavelength-specific absorbance data obtained from a detection area reset as a result of correction of an error of distance of the optical sensor 1010. In embodiments, the wavelength-specific absorbance data may be corrected by applying a wavelength-specific absorbance correction coefficient obtained according to the correction of an error of distance of the optical sensor 1010 to the wavelength-specific absorbance data obtained by the optical sensor 1010, and estimate the biometric information using the corrected wavelength-specific absorbance data.

In embodiments, the processor 1020 may correct the biometric information estimation model based on the error of the distance between the light source 1011 and the detector 1012 or the state of the light source being corrected. Here, the biometric information estimation model may represent the correlation between the wavelength-specific absorbance and the biometric information, and may be generated as a linear or non-linear function equation through machine learning, a neural network, artificial intelligence, or the like using wavelength-specific absorbance and estimated biometric information values acquired from a plurality of users as training data.

For example, the processor 1020 may correct the biometric information estimation model based on the degree of change in the distance between the light source 1011 and the detector 1012 of the optical sensor 1010 compared to the preset distance of the present optical sensor and/or the correlation between the degree of correction of the light source state and a coefficient and/or offset of each variable of the biometric information estimation model. For example, an equation that represents the degree of change of the distance and/or the correlation between the degree of correction of the light source state and a coefficient and/or offset of each variable of the biometric information estimation model may be predefined, and the coefficient and/or offset of the biometric information estimation model may be corrected using the equation.

For example, Equation 8 below is a linear function equation that may be used to simply define the biometric information estimation model. However, this is merely an example, and embodiments are not limited thereto.

$$y=ax+b \hspace{2cm} \text{Equation 8}$$

Here, y denotes an estimated biometric information value to be obtained and x denotes, for example, absorbance. a denotes a coefficient of the absorbance and b denotes the offset. a and b are predefined values. For example, the offset b due to the correction of an error of distance may be corrected using the linear relationship that represents the correlation between the offset b and the degree of change in the distance.

In another example, the biometric information estimation model may be predefined step by step according to the degree of change in the distance between the light source and the detector, and the biometric information may be estimated by selecting the biometric information estimation model that corresponds to the degree of change in the distance.

The input interface 1030 may receive a command and/or data to be used in each component, for example, the processor 1020, of the apparatus 1000 for from the user or an external device. The input interface 1030 may include a microphone, a mouse, a keyboard, a touch screen, and/or a digital pen (stylus pen, etc.), but embodiments are not limited thereto.

The storage 1040 may store preset information for correction of an error of the optical sensor 1010, error correction information of the optical sensor 1010 (e.g., reset coordinate information for each light source, brightness of each light source, correction coefficient, and the like), preset information for biometric information estimation, for example, user characteristic information, such as a health condition, gender, age, or the like of the user, the biometric information estimation model, a relationship for correcting the biometric information estimation model, and the like. Also, the storage 1040 may store data generated and/or processed by various components of the apparatus 1000. As described above, the storage 1040 may include a storage medium, such as a flash memory type, a hard disk type, a multimedia card micro type, a card type memory (e.g., a SD or XD memory), a RAM, a SRAM, a ROM, an EEPROM, a PROM, a magnetic memory, a magnetic disk, an optical disk, and the like, but embodiments are not limited thereto.

The output interface 1050 may externally output the data generated or processed by various components of the apparatus 1000. For example, the output interface 1050 may include an acoustic output device to externally output an acoustic signal. An acoustic output module may include a speaker and/or a receiver.

Also, the output interface 1050 may include a display device to visually provide data. The display device may include a display, a hologram device, or a projector. The display device may include a touch circuitry set to sense a touch and/or a sensor circuitry (pressure sensor, etc.) set to measure a magnitude of a force generated by a touch.

Also, the output interface 1050 may include a haptic module to output data through tactile sensation or vibration. The haptic module may convert an electrical signal into a mechanical stimulation (vibration, motion, etc.) or an electrical stimulation that the user is able to recognize through a tactile sensation or kinesthetic sensation. The haptic module may include a motor, a piezoelectric element, and/or an electrical stimulation device.

The communication interface 1060 may communicate with an external device to transmit the data generated and/or processed by each component of the apparatus 1000 to the external device, and may receive data to be used in the apparatus 1000 from the external device. The external device may include an information processing device, such as a smartphone, a tablet personal computer (PC), a desktop PC, a laptop PC, or the like.

The communication interface 1060 may communicate with the external device by using various wired or wireless communication techniques including Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, the communication techniques are not limited thereto.

Figure 11:
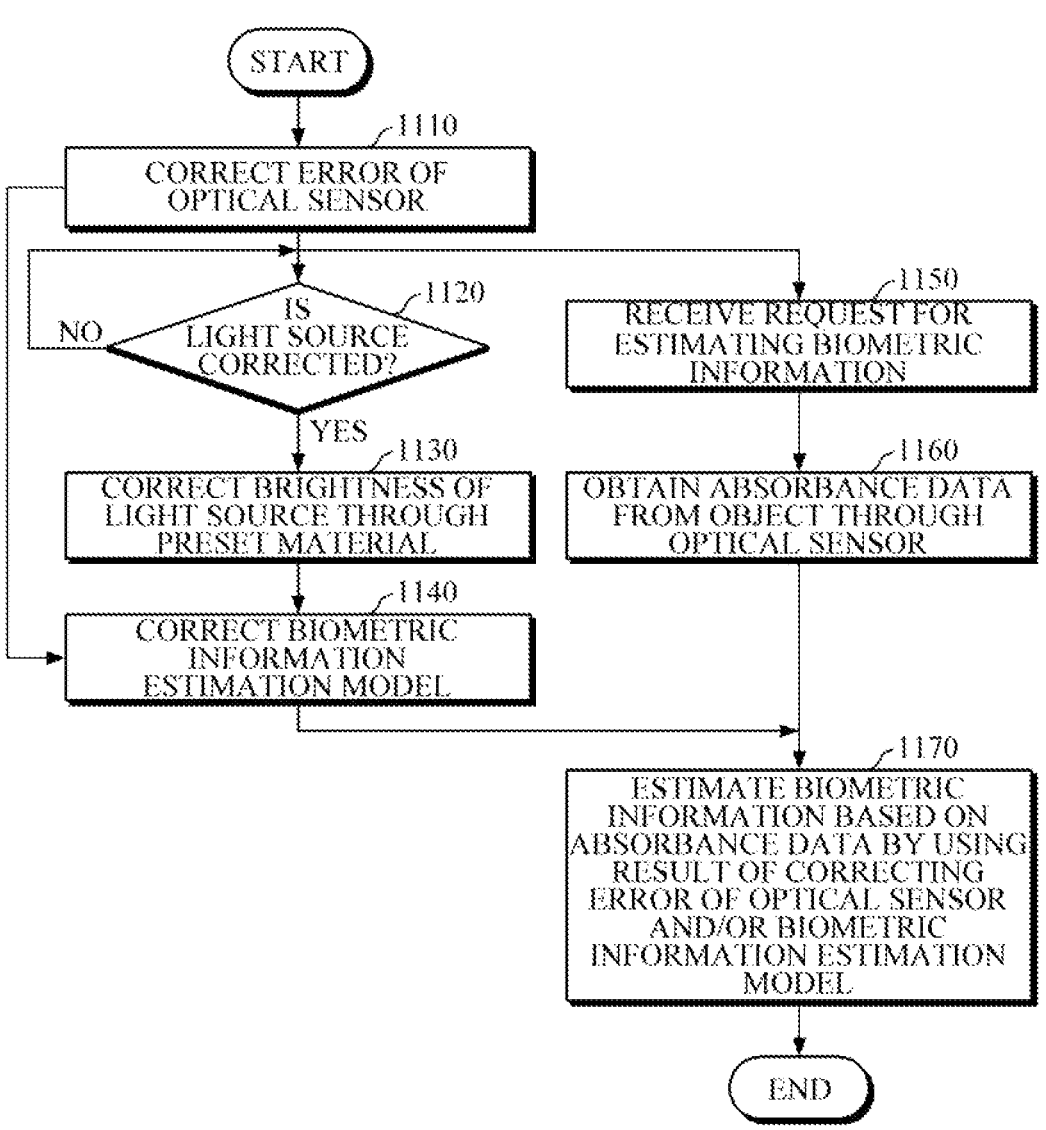
FIG. 11 is a flowchart illustrating a method of estimating biometric information according to an embodiment.

FIG. 11 is a flowchart illustrating a method of estimating biometric information according to an embodiment.

FIG. 11 illustrates an embodiment of a method performed by the apparatus 1000, which has been described above, and thus will be briefly described below.

First, at operation 1110 an error of distance of a mounted optical sensor may be corrected. Operation 1110 may be performed at least one time prior to using the apparatus 1000 for estimating biometric information, and may be performed even after the apparatus 1000 is used if necessary or desired. Based on the correction of the error of distance of the optical sensor being completed, a biometric information estimation model may be corrected at operation 1140.

Based on the correction of the error of distance of the optical sensor being completed, correction of a light source state and biometric information estimation may be performed regardless of the time sequence each time a corresponding condition is satisfied. For example, at operation 1120, it may be determined whether the correction condition of the light source state is satisfied. Based on the correction condition being satisfied, at operation 1130 a brightness of the light source may be corrected using a preset material, and at operation 1140 a biometric information estimation model may be corrected based on a result of correcting the error of the optical sensor and/or a result of correcting the brightness of the light source. In addition, based on a request for estimating biometric information being received at operation 1150, absorbance data may be obtained from an object through the optical sensor at operation 1160, and biometric information may be estimated using the result of correcting the error of the optical sensor and the biometric information estimation model at operation 1170. As such, accuracy of estimating biometric information may be improved by frequently correcting the state of the light source and/or the biometric information estimation model before and after biometric information estimation.

Figure 12:
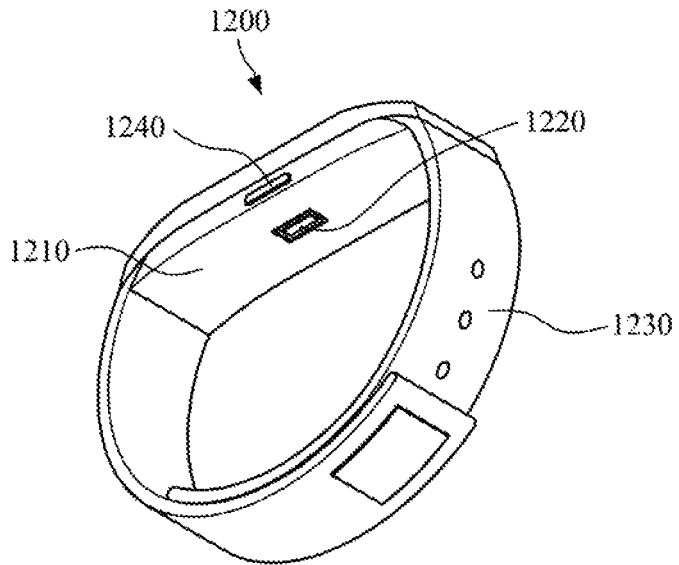
FIG. 12 is a diagram illustrating a wearable device including an apparatus for estimating biometric information. according to an embodiment.

FIG. 12 is a diagram illustrating a wearable device including an apparatus for estimating biometric information. As illustrated, a wearable device 1200 of one example embodiment may be a smartwatch that a user can wear. However, the wearable device 1200 is not limited thereto, and may include a smart band, a smart necklace, a smart ring, an ear-type wearable device, and the like. The wearable device 1200 may include various example embodiments of the apparatus 1000 described above.

Referring to FIG. 12, the wearable device 1200 includes a main body 1210 and a strap 1230. The main body 1210 may be worn with the strap 1230 around a user's wrist. The main body 1210 may include the apparatus 1000 of the wearable device 1200 for estimating biometric information and configurations to perform other functions.

A battery may be embedded in the main body 1210 or the strap 1230 to supply power to the wearable device. The strap 1230 may be made of a flexible material to conform to a user's wrist. The strap 1230 may include a first strap and a second strap that are separate from each other. Each of one ends of the first strap and the second strap may be connected to each of the both ends of the main body 1210, and the first strap and the second strap may be fastened to each other via a fastener. In this case, the fastener may include a magnet fastener, a Velcro fastener, a pin fastener, but embodiments are not limited thereto. In addition, the strap 1230 may be or include an integrated piece, such as a band.

An optical sensor 1220 may be mounted on one surface of the main body 1210, and a processor disposed in the main body 1210 may be electrically connected to the optical sensor 1220. The optical sensor 1220 may include a light source and a detector. The light source may include an LED, and the detector may include an image sensor, one or more photodiodes, a photodiode array, or the like. The processor may estimate biometric information using absorbance data acquired from an object through the optical sensor 1220.

In addition, as described above, the processor may correct an error of a distance between the light source and the detector of the optical sensor 1220 prior to using the wearable device 1200. When a preset condition, such as prior to biometric information estimation, a predetermined period, a user's request, or in contact with a preset material (e.g., being placed on a charger coated with a preset material), is satisfied, the state of the light source, such as the brightness of the light source, may be corrected using a preset material, and a biometric information estimation model may be corrected.

Also, the main body 1210 may include a storage to store data generated and/or processed by the wearable device 1200 and a communication interface to transmit and received data to and from an external device.

A manipulator 1240 may be mounted on one side of the main body 1210 to receive a control command of the user and transmit the received control command to the processor. The manipulator 1240 may include a power button to input a command to turn on/off the wearable device 1200.

Also, a display may be mounted on the front surface of the main body 1210, and the display may include a touch screen enabling touch input. The display may receive a touch input of the user, transmit the received touch input to the processor, and display a processing result of the processor.

Figure 13:
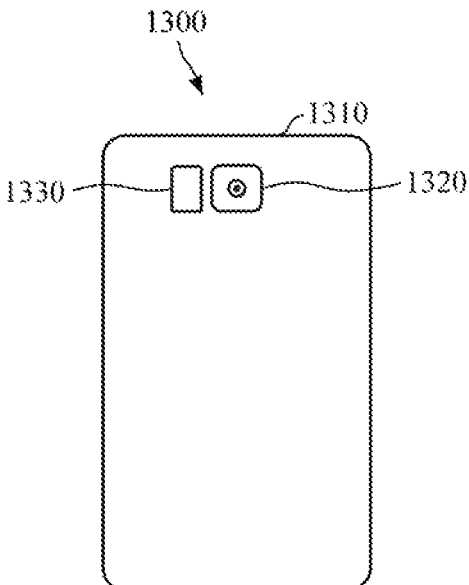
FIG. 13 is a diagram illustrating a mobile device including an apparatus for estimating biometric information, according to an embodiment.

FIG. 13 is a diagram illustrating a mobile device including an apparatus for estimating biometric information. As illustrated in FIG. 13, the mobile device 1300 may be a smartphone, but embodiments are not limited thereto and may include a tablet PC or the like. The mobile device 1300 may include various example embodiments of the apparatus 1000 for estimating biometric information described above.

The mobile device 1300 may have an optical sensor 1330 mounted on a rear surface of a main body 1310. The optical sensor 1330 may include a light source including an LED or the like, and a detector including an image sensor, a photodiode array, or the like.

A processor may be disposed inside the main body 1310 of the mobile device 1300, and the processor may be electrically connected to the optical sensor 1330 and estimate biometric information using absorbance data of an object received from the optical sensor 1330.

In addition, as described above, the processor may correct an error of a distance between the light source and the detector of the optical sensor 1330 prior to using the mobile device 1300. When a preset condition, such as prior to biometric information estimation, a predetermined period, a user's request, or being placed on a preset material (e.g., charger), is satisfied, the state of the light source, such as the brightness of the light source, may be corrected using a preset material, and a biometric information estimation model may be corrected.

A camera module 1320 may be disposed on the rear surface of the main body 1310 of the mobile device 1300. The camera module 1320 may capture a still image or record a video. The camera module 1320 may include a lens assembly including one or more lenses, image sensors, image signal processors and/or flashes.

A display may be mounted on the front surface of the main body 1310 of the mobile device 1300. The display may visually output various data generated and/or processed in the mobile device 1300 and may include a touch screen to receive a touch input.

Figure 14:
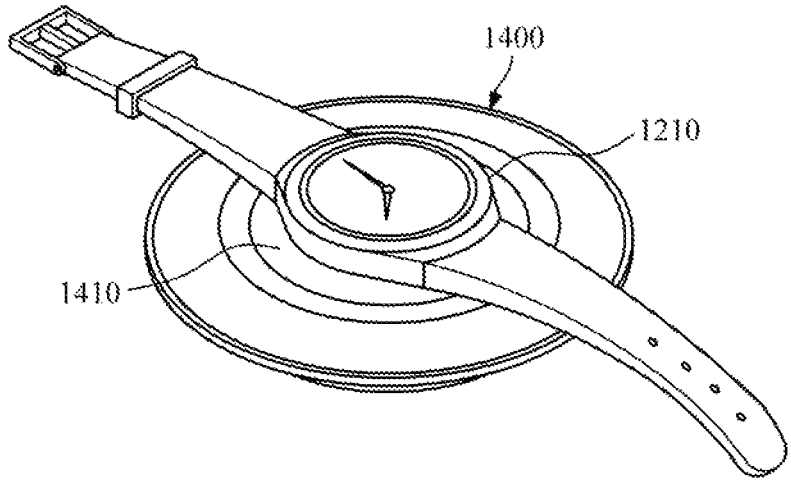
FIG. 14 is a diagram illustrating a wearable device placed on a charger coated with a reflective material, according to an embodiment.

FIG. 14 is a diagram illustrating a wearable device placed on a charger coated with a reflective material.

Referring to FIG. 14, a main body of a charger 1400 may have a circular shape with a flat upper surface. However, the main body is not limited thereto, and may have various shapes, such as a rectangular shape, a pentagonal shape, a triangular shape, a hexagonal shape, etc., and the upper surface may have a structure that can be naturally positioned at a chargeable area of the wearable device 1200 when the wearable device 1200 is placed thereon.

A reflective material may be disposed or applied on the upper surface 1410 of the charger 1400, that is, the surface with which the wearable device 1200 makes contact when placed thereon. The reflective material may be a diffuse reflection material having a reflectance of 1% to 99T, and may include barium sulfate (BaSo4), Teflon (PTEF), etc.

An optical sensor may be disposed on the rear surface of the wearable device 1200, that is, a surface in contact with the upper surface 1410 of the charger 1400, and the processor of the wearable device 1200 may check whether the wearable device 1200 is placed on the charger 1400 when the error correction time is reached, for example when a user's request is received, when a predetermined time period is reached, or when a request for estimating biometric information is received. If the wearable device 1200 is placed on the charger 1410, the processor may correct an error of the optical sensor as described above, and otherwise, output visual information on a display to guide the user to place the wearable device on the charger, or output audio information using an audio output device.

The example embodiments can be implemented as computer readable codes in a computer readable record medium. The computer readable recording medium includes all types of recording media in which computer readable data can be stored.

Examples of the computer readable recording medium include a ROM, a RAM, a compact disc (CD)-ROM, a magnetic tape, a floppy disk, and an optical disk, etc. Also, an example embodiment may be written as a computer program transmitted over a computer-readable transmission medium, such as a carrier wave. Further, the computer readable recording medium may be distributed to computer systems over a network in which computer readable codes may be stored and executed in a distributed manner.<Functional programs, codes and code segments constituting the computer program can be easily inferred by a skilled computer programmer in the art.

It will be apparent after an understanding of the disclosure that various changes in form and details may be made in these examples without departing from the spirit and scope of the claims and their equivalents. The examples described herein are to be considered in a descriptive sense only, and not for purposes of limitation.

The invention claimed is:

1. A method of correcting an error of an optical sensor which includes a light source and a detector, the method comprising:
   adjusting a brightness of the light source to a preset brightness;
   controlling the light source to emit light to a preset material;
   acquiring preset material data corresponding to the emitted light and the preset material using the detector; and
   correcting, by using the acquired preset material data, an error of a distance between the light source and the detector based on a difference between a first amount of light received at a first point of the detector and a second amount of light received at a second point of the detector, or based on a gradation of an image obtained by the detector,
   wherein the correcting of the error comprises: detecting a change in the distance between the light source and the detector with respect to a preset distance; and
   correcting the error of the distance between the light source and the detector based on the detected change in the distance,
   wherein the correcting of the error comprises:
   obtaining a slope corresponding to the first amount of light and the second amount of light; and detecting the change in the distance between the light source and the detector based on the obtained slope and a preset slope,
   wherein the correcting of the error comprises:
   obtaining a first slope between X-coordinate points corresponding to the first point and the second point, and a second slope between Y-coordinate points corresponding to the first point and the second point; and
   detecting the change in the distance between the light source and the detector based on the obtained first slope and the obtained second slope.

2. The method of claim 1, wherein the correcting of the error comprises resetting coordinates of a detection area of the detector with respect to the light source based on the detected change in the distance between the light source and the detector.

3. The method of claim 1, wherein the emitting of the light comprises emitting additional light from an additional light source, wherein the additional light has a same wavelength as the light emitted from the light source, and
   wherein the correcting of the error comprises:
   detecting contour lines at positions corresponding to preset contour points from the preset material data;
   obtaining a contour slope between the detected contour lines; and
   detecting the change in the distance between the light source and the detector based on the obtained contour slope and a preset contour slope.

4. The method of claim 3, wherein the correcting of the error comprises:
   detecting a vector between the light source and the additional light source, and
   moving coordinates of a detection area of the detector with respect to the light source along the detected vector based on the change in the distance between the light source and the detector.

5. An apparatus for correcting an error of an optical sensor comprising a light source and a detector, the apparatus comprising:
   at least one processor configured to:
   adjust a brightness of the light source to a preset brightness,
   drive the light source to emit light to a preset material, and
   correct, by using preset material data obtained by the detector, an error of a distance between the light source and the detector based on a difference between a first amount of light received at a first point of the detector and a second amount of light received at a second point of the detector, or based on a gradation of an image obtained by the detector,
   wherein the at least one processor is further configured to:
   correct a change in the distance between the light source and the detector with respect to a preset distance, and
   correct the error of the distance between the light source and the detector based on the detected change in the distance,
   wherein the at least one processor is further configured to:
   obtain a slope corresponding to the first amount of light and the second amount of light, and
   detect the change in the distance between the light source and the detector based on the obtained slope and a preset slope,
   wherein the at least one processor is further configured to:
   obtain a first slope between X-coordinate points corresponding to the first point and the second point, and a second slope corresponding to the first point and the second point, and a second slope between Y-coordinate points correspond-
ing to the first point and the second point, and detect the change in the distance between the light source
and the detector based on the obtained first slope and
the obtained second slope.

6. The apparatus of claim 5, further comprising a storage configured to store preset information including at least one of a preset brightness of a light source of a preset optical sensor, position information about preset points of the detector, a preset slope corresponding to the preset points, a preset contour slope corresponding to the preset points, and a preset distance between the light source and an image sensor.

7. The apparatus of claim 5, wherein the at least one processor is further configured to reset coordinates of a detection area of the detector with respect to the light source based on the detected change in the distance between the light source and the detector.

8. The apparatus of claim 5, wherein the at least one processor is further configured to:

drive an additional light source to emit additional light,
wherein the additional light has a same wavelength as
the light emitted from the light source, detect contour lines at positions corresponding to preset
contour points from the preset material data, obtain a contour slope between the detected contour lines,
and detect the change in the distance between the light source
and the detector based on the obtained contour slope
and a preset contour slope.

9. The apparatus of claim 8, wherein the at least one processor is further configured to:

detect a vector between the light source and the additional
light source, and move coordinates of a detection area of the detector with
respect to the light source along the detected vector
based on the change in the distance between the light
source and the detector.

10. A method of correcting an error of an optical sensor which includes a light source, a first detector, and a second detector, the method comprising:

controlling the light source to emit light to a preset
material;

adjusting a brightness of the light source so that a mea-
surement value of the first detector is same as a first
measurement value;

obtaining a second measurement value from the second
detector;

calculating a slope based on a difference between the first
measurement value and the second measurement value;
and correcting an error of a distance between the light source
and the second detector based on the calculated slope, wherein the correcting of the error comprises obtaining a
correction coefficient for the second measurement
value based on the calculated slope, wherein the correcting of the error comprises:

determining a length of an optical path between the light
source and the second detector; and obtaining the correction coefficient for the second mea-
surement value based on the determined length of the
optical path.

11. The method of claim 10, wherein the correcting of the error comprises:

calculating the distance between the light source and the
second detector based on the calculated slope; and determining the length of the optical path based on the
calculated distance.

12. The method of claim 10, wherein the correcting of the error comprises:

calculating a ratio between a preset slope of a preset
optical sensor and the calculated slope; and determining the length of the optical path based on the
calculated ratio.

* * * * *